US010251636B2

(12) United States Patent
Hess et al.

(10) Patent No.: US 10,251,636 B2
(45) Date of Patent: Apr. 9, 2019

(54) DEVICES AND METHODS FOR CLEANING A SURGICAL DEVICE

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Daniel J. Mumaw, Liberty Township, OH (US); Craig T. Gates, West Chester, OH (US); Douglas E. Withers, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 391 days.

(21) Appl. No.: 14/864,118

(22) Filed: Sep. 24, 2015

(65) Prior Publication Data

US 2017/0086815 A1 Mar. 30, 2017

(51) Int. Cl.
*A61B 17/04* (2006.01)
*A61B 17/29* (2006.01)
(Continued)

(52) U.S. Cl.
CPC .......... *A61B 17/0469* (2013.01); *A61B 17/29* (2013.01); *A61B 90/70* (2016.02);
(Continued)

(58) Field of Classification Search
CPC ................ A61B 17/0469; A61B 17/29; A61B 2017/00473; A61B 2017/00477;
(Continued)

(56) References Cited

U.S. PATENT DOCUMENTS

| 3,043,309 A | 7/1962 | McCarthy |
| 3,358,676 A | 12/1967 | Frei et al. |

(Continued)

FOREIGN PATENT DOCUMENTS

| AU | 2013200993 A1 | 3/2013 |
| DE | 101 49 421 A1 | 4/2003 |

(Continued)

OTHER PUBLICATIONS

International Search Report dated Mar. 21, 2011; International Application No. PCT/US2010/051812 (7 pages).

(Continued)

*Primary Examiner* — Ashley L Fishback
(74) *Attorney, Agent, or Firm* — Mintz Levin Cohn Ferris Glovsky and Popeo, P.C.

(57) ABSTRACT

Devices and methods for cleaning a surgical device, and or end effectors associated with the device, are provided. In one exemplary embodiment, a surgical device includes a housing, a plurality of shafts extending distally from the housing, a port disposed at a proximal end of the shafts to form a proximal compartment and an end effector receiver disposed at a distal end of the shafts to form a distal compartment. A fluid and/or a vacuum source can be supplied at the port, through the proximal compartment and shafts, and to the distal compartment. The supplied fluid or vacuum source can be effective to remove fluid and/or tissue from the distal compartment. A plurality of seals can be provided on an outer-most shaft in the compartments to seal fluid from the compartments from entering a housing and/or an outside environment. Other devices and exemplary methods are also provided.

19 Claims, 8 Drawing Sheets

(51) Int. Cl.
*A61B 17/00* (2006.01)
*A61B 90/70* (2016.01)

(52) U.S. Cl.
CPC .............. *A61B 2017/00473* (2013.01); *A61B 2017/00477* (2013.01); *A61B 2017/2931* (2013.01); *A61B 2017/2948* (2013.01); *A61B 2217/005* (2013.01); *A61B 2217/007* (2013.01)

(58) Field of Classification Search
CPC .... A61B 2017/2931; A61B 2017/2948; A61B 2217/005; A61B 2217/007
See application file for complete search history.

(56) References Cited

U.S. PATENT DOCUMENTS

| | | |
|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 4,950,238 A | 8/1990 | Sullivan |
| 5,052,402 A | 10/1991 | Bencini et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,716,326 A | 2/1998 | Dannan |
| 5,762,255 A | 6/1998 | Chrisman et al. |
| 5,792,165 A | 8/1998 | Klieman et al. |
| 5,810,877 A | 9/1998 | Roth et al. |
| 5,881,615 A | 3/1999 | Dahl et al. |
| 5,928,263 A | 7/1999 | Hoogeboom |
| 5,980,455 A | 11/1999 | Daniel et al. |
| 6,024,748 A | 2/2000 | Manzo et al. |
| 6,059,719 A | 5/2000 | Yamamoto et al. |
| 6,099,537 A | 8/2000 | Sugai et al. |
| 6,159,200 A | 12/2000 | Verdura et al. |
| 6,309,397 B1 | 10/2001 | Julian et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,128,643 B2 | 3/2012 | Aranyi et al. |
| 8,182,414 B2 | 5/2012 | Handa et al. |
| 8,187,166 B2 | 5/2012 | Kuth et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,623,011 B2 | 1/2014 | Spivey |
| 8,636,648 B2 | 1/2014 | Gazdzinski |
| 8,721,539 B2 | 5/2014 | Shohat et al. |
| 8,764,735 B2 | 7/2014 | Coe et al. |
| 8,845,661 B2 | 9/2014 | D'Arcangelo et al. |
| 8,906,043 B2 | 12/2014 | Woodard, Jr. et al. |
| 9,113,861 B2 | 8/2015 | Martin et al. |
| 9,142,527 B2 | 9/2015 | Lee et al. |
| 9,282,879 B2 | 3/2016 | Farin et al. |
| 9,308,011 B2 | 4/2016 | Chao et al. |
| 9,408,628 B2 | 8/2016 | Altamirano |
| 9,451,937 B2 | 9/2016 | Parihar |
| 9,468,454 B2 | 10/2016 | Johnson et al. |
| 2001/0051766 A1 | 12/2001 | Gazdzinski |
| 2003/0060702 A1 | 3/2003 | Kuth et al. |
| 2003/0114731 A1 | 6/2003 | Cadeddu et al. |
| 2004/0093039 A1 | 5/2004 | Schumert |
| 2004/0133235 A1 | 7/2004 | Bacher |
| 2004/0152941 A1 | 8/2004 | Asmus et al. |
| 2005/0033354 A1 | 2/2005 | Montalvo et al. |
| 2005/0085697 A1 | 4/2005 | Yokoi et al. |
| 2005/0119640 A1 | 6/2005 | Sverduk et al. |
| 2005/0131396 A1 | 6/2005 | Stanczak et al. |
| 2005/0165449 A1 | 7/2005 | Cadeddu et al. |
| 2005/0215983 A1 | 9/2005 | Brock |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0149135 A1 | 7/2006 | Paz |
| 2006/0184161 A1 | 8/2006 | Maahs et al. |
| 2006/0190035 A1 | 8/2006 | Hushka et al. |

(56) References Cited

U.S. PATENT DOCUMENTS

| | | |
|---|---|---|
| 2006/0195015 A1 | 8/2006 | Mullick et al. |
| 2006/0229592 A1 | 10/2006 | Yokoi et al. |
| 2006/0258905 A1 | 11/2006 | Kaji et al. |
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0188831 A1* | 8/2008 | Bonnette ............. A61B 17/22 604/524 |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0209947 A1 | 8/2009 | Gordin et al. |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0259325 A1 | 10/2012 | Houser et al. |
| 2012/0316575 A1 | 12/2012 | Farin et al. |
| 2013/0085341 A1 | 4/2013 | Nobis et al. |
| 2013/0138091 A1 | 5/2013 | Coe et al. |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0171972 A1 | 6/2014 | Martin |
| 2014/0243799 A1 | 8/2014 | Parihar |
| 2014/0243800 A1 | 8/2014 | Parihar |
| 2014/0277018 A1 | 9/2014 | Parihar |
| 2014/0378953 A1 | 12/2014 | Coe et al. |
| 2015/0088191 A1 | 3/2015 | Coe et al. |
| 2015/0230784 A1 | 8/2015 | Shelton, IV et al. |
| 2016/0135872 A1 | 5/2016 | Minnelli et al. |

FOREIGN PATENT DOCUMENTS

| | | |
|---|---|---|
| EP | 1 709 900 A1 | 10/2006 |
| EP | 2883508 | 6/2015 |
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |

OTHER PUBLICATIONS

International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
U.S. Application filed Oct. 9, 2009 for U.S. Appl. No. 12/576,529 (18 pages).
European Search Report for EP Application No. 16190462.8 dated Dec. 12, 2016 (8 pages).
International Search Report for PCT Application No. PCT/US2016/052030 dated Dec. 12, 2016 (7 pages).

* cited by examiner

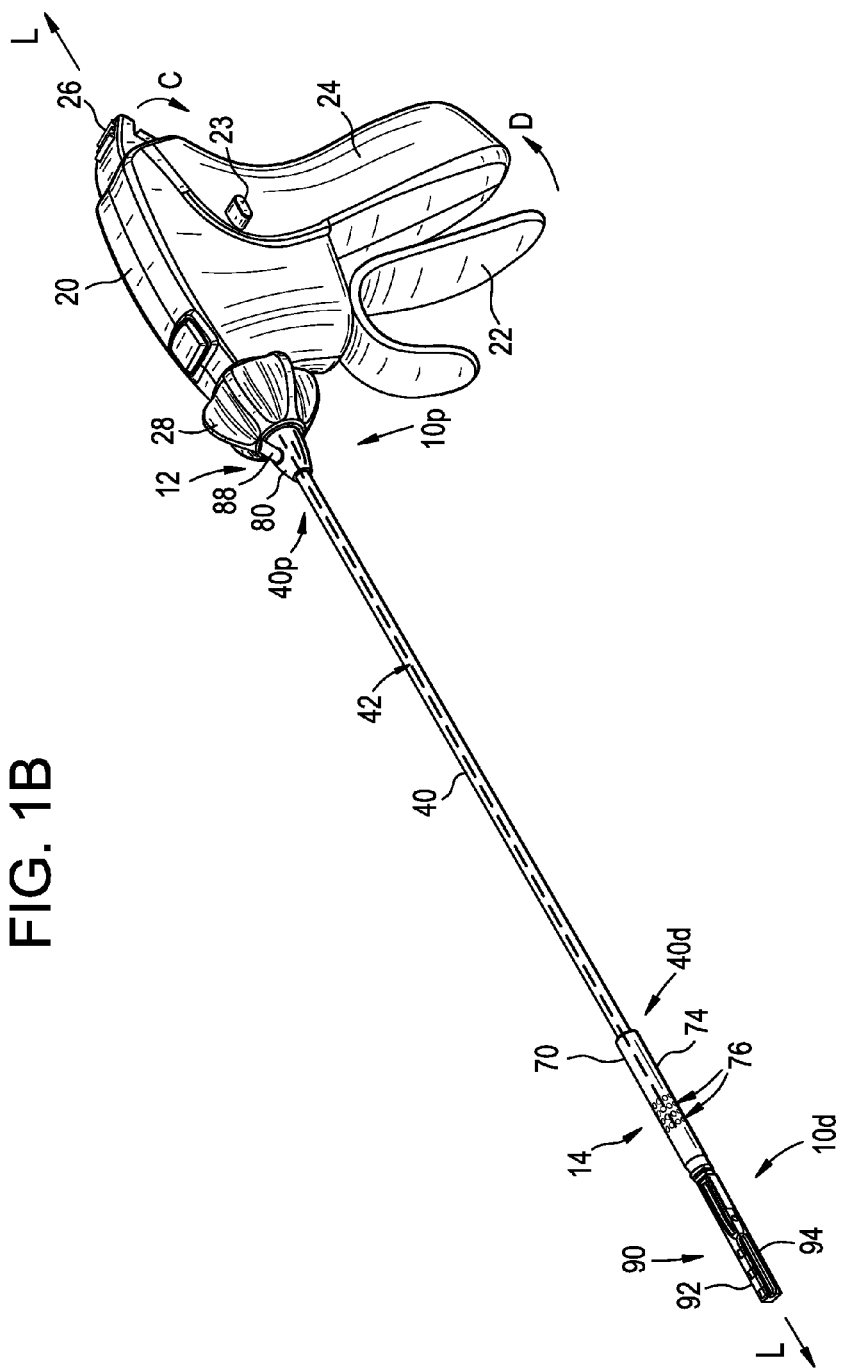

FIG. 2A
FIG. 2B
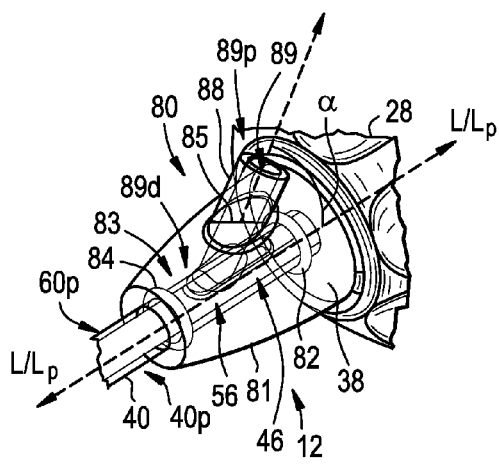
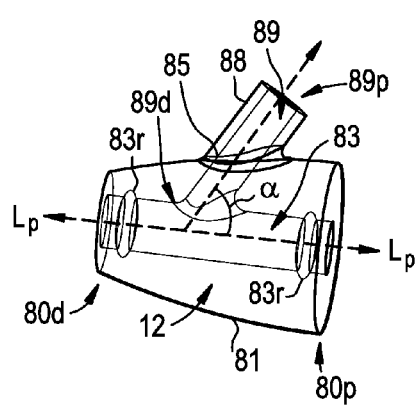
FIG. 2C
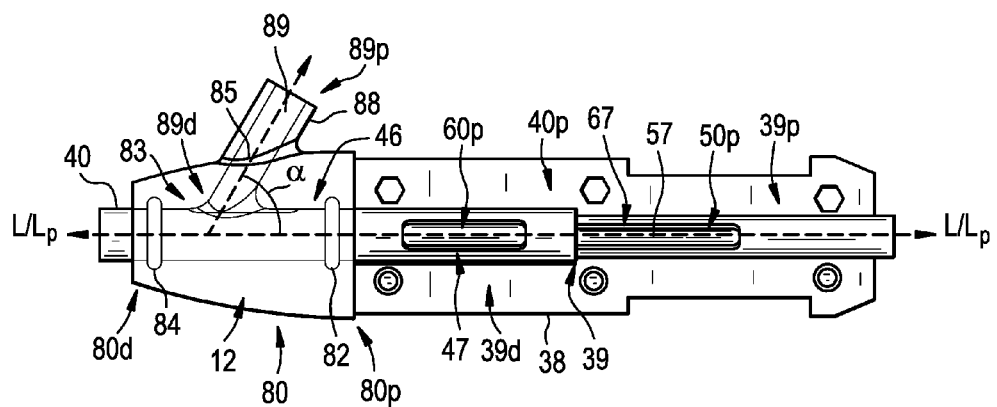

DEVICES AND METHODS FOR CLEANING A SURGICAL DEVICE

FIELD

The present disclosure relates to devices and methods for use in laparoscopic and endoscopic procedures, and more particularly relates to devices and methods for cleaning a surgical device.

BACKGROUND

Minimally invasive surgical techniques are often preferred over traditional open surgeries because the recovery time, pain, and surgery-related complications are typically less with minimally invasive techniques. Many types of procedures can be performed using minimally invasive techniques, with various end effectors or tools being disposed at a distal end of the device to perform particular tasks. For example, an end effector can be jaws for grasping tissue, or an end effector can be a suturing head for applying suture to tissue. During the course of operating these end effectors, various fluids (e.g., blood) and tissue fragments can impede the field of view of the operator, for instance by blocking or blurring an endoscope or laparoscope disposed at the surgical site, and/or impede the progress of the end effector being used. When using a suturing head, for example, as a needle is passed back-and-forth between jaws, the fluid and tissue fragments that may exist at the surgical site can make it difficult to see the needle to know which jaw it is in and to know the general progress of the stitching procedure. Fragments and fluid may also impede the reception of the needle by either or both of the jaws. Some of the fluid and tissue may be more easily cleaned by applying a vacuum force to the area in need of cleaning, while other fluid and tissue may be more easily cleaned by applying an irrigation force.

Further, some existing devices are also not well equipped to be reused, whether with the same or different end effectors. Thus, a new device may be used for each new patient and/or with the same patient when two or more end effectors are needed during the course of a single surgical procedure. This helps protect the patient by providing a new, sterile device, but leads to increases in cost and waste. Additionally, for some existing devices, the devices are not well-equipped to interchangeably use different types of end effectors. Thus, it may be difficult to use an end effector such as jaws for grasping tissue with the same base device as an end effector that uses a suturing head to stitch tissue.

Accordingly, there is a need for minimally invasive devices and methods that allow a surgical device to be reused and can be used with multiple types of end effectors. There is also a need for a surgical device capable of being cleaned using multiple cleaning methods, e.g., interchangeably applying vacuum and irrigation forces as desired.

SUMMARY

Devices and methods are generally provided that allow a surgical device to be cleaned and reused, whether with the same or with different end effectors. The device generally provides the ability to apply both suction and irrigation forces to a distal end of the surgical device, and an end effector if one is coupled to the distal end of the device, to clean the distal end of the device and/or the end effector. The suction and irrigation forces can be supplied through a port or sealed-off compartment or chamber (e.g., sealed-off at least at one location) at a proximal end of the device, through a shaft of the device, and to the distal end of the device in another compartment or chamber that is also sealed-off at least at one location. Notably, the term sealed-off as used herein does not necessarily mean the chamber is fully sealed off, but just that a seal is formed at least at one location where a seal is placed for the purpose of preventing fluid from passing directly adjacent to the seal. When using suction, a suction or vacuum force can be supplied at the port to draw fluid and tissue from the distal chamber, through the shaft, to the port, and out of the device. When using irrigation, a fluid can be supplied from the port, through the shaft, and to the distal chamber to drive fluid and/or tissue out of blow-out ports formed in the distal chamber. A variety of end effectors can be used in conjunction with the devices provided for herein, including but not limited to grasping jaws and a suturing head.

In one exemplary embodiment, a surgical device includes a housing, an outer shaft that is coupled to and extends distally from the housing, a port coupled to a proximal portion of the outer shaft, an end effector receiver removably coupled to a distal portion of the shaft, and first, second, and third seals. The outer shaft has a sidewall and an inner lumen that extends between the proximal and distal portions. Further, each of the proximal and distal portions of the outer shaft has at least one opening formed in the sidewall. A relief channel is formed in the port. The relief channel has a valve associated with it, with the relief channel being in fluid communication with the opening(s) formed in the sidewall of the proximal portion of the outer shaft. The end effector receiver has a sidewall with one or more openings formed in it and an inner lumen that is in fluid communication with the inner lumen of the outer shaft. The first seal is disposed on and around the outer shaft, disposed proximal of the opening (s) formed in the sidewall of the proximal portion of the outer shaft. The second seal is disposed on and around the outer shaft and disposed distal of the opening(s) formed in the sidewall of the proximal portion of the outer shaft. The third seal is disposed on and around the distal portion of the outer shaft.

In some exemplary embodiments, the surgical device includes an inner shaft that is disposed within the inner lumen of the outer shaft. The inner shaft can be configured to translate relative to the outer shaft along a longitudinal axis of the outer shaft. The inner shaft can have a sidewall and an inner lumen that extends between proximal and distal portions of the inner shaft. Each of the proximal and distal portions of the inner shaft can include at least one opening formed in the sidewall. The inner shaft can have a locked configuration (sometimes referred to as a cleaning configuration). In the locked configuration, at least one opening formed in the sidewall of the proximal portion of the inner shaft can be in fluid communication with the opening(s) formed in the sidewall of the proximal portion of the outer shaft, and at least one opening formed in the sidewall of the distal portion of the inner shaft can be in fluid communication with the inner lumen of the end effector receiver. In an unlocked configuration of the device, the end effector receiver can be configured to be decoupled from the outer shaft.

The device can also include an intermediate shaft that is disposed between the outer shaft and the inner shaft, and is configured to translate relative to the outer shaft along the longitudinal axis of the outer shaft. The intermediate shaft can have a sidewall and an inner lumen that extends between proximal and distal portions of the intermediate shaft. Each of the proximal and distal portions of the intermediate shaft can include at least one opening formed in the sidewall. In the aforementioned locked (or cleaning) configuration, a distal end of the inner shaft can be disposed at or distal of a distal end of the intermediate shaft, with the distal end of the intermediate shaft being disposed distal of a distal end of the outer shaft. Further, in the locked configuration, the opening(s) formed in the sidewall of the proximal portion of the intermediate shaft can be in fluid communication with at least one of the openings formed in the sidewalls of the proximal portions of the outer and inner shafts, and the opening(s) formed in the sidewall of the distal portion of the intermediate shaft can be in fluid communication with the opening(s) formed in the sidewall of the distal portion of the inner shaft and the inner lumen of the end effector receiver. In some embodiments, the end effector receiver can include a coupler disposed within the inner lumen of the end effector receiver. The coupler can include a proximal portion that is coupled to the intermediate shaft in the locked configuration and a distal portion that is configured to receive an end effector such that the end effector is operable by one or more components of the housing when coupled to the distal portion of the coupler.

A screen can be disposed over or in the opening(s) formed in the sidewall of the end effector receiver. The screen can include two screens, with the two screens being offset with respect to each other such that openings in the first screen are partially aligned with the openings in the second screen. The first and second screens can be spaced a distance radially apart from each other.

The first and second fluid seals can be disposed within the port. The relief channel of the port can be disposed at an oblique angle with respect to the outer shaft. More particularly, in some embodiments, an end of the channel that is disposed adjacent to the opening(s) formed in the sidewall of the proximal portion of the outer shaft can be more distal than an opposed end of the channel that is disposed radially outward from the outer shaft. Still further, in some embodiments, a suturing head can be coupled to the end effector receiver.

In another exemplary embodiment, a surgical device includes a housing, a shaft that is coupled to and extends distally from the housing, an end effector receiver that is coupled to the shaft, distal of the housing, and a port that is coupled to the shaft. The shaft has a sidewall, an inner lumen, and at least one opening formed in the sidewall such that the opening(s) is in fluid communication with the inner lumen. The end effector receiver has a sidewall with one or more openings formed in it, as well as an inner lumen that is in fluid communication with the opening(s) formed in the sidewall of the shaft. The port has a relief channel formed in it that is in fluid communication with the opening(s) formed in the sidewall of the shaft. The port is configured to be operated in two configurations. In the first configuration, a vacuum force can be applied to the end effector receiver to move at least one of fluid and tissue from the end effector receiver to and out the relief channel of the port. In the second configuration, fluid is passed from the relief channel of the port to the end effector receiver to advance at least one of fluid and tissue disposed within the end effector receiver out of the one or more openings formed in the sidewall of the end effector receiver.

In some embodiments, a screen can be disposed over or in the opening(s) formed in the sidewall of the end effector receiver. The screen can include two screens, with the two screens being offset with respect to each other such that openings in the first screen are partially aligned with the openings in the second screen. The first and second screens can be spaced a distance radially apart from each other.

The opening(s) formed in the sidewall of the shaft can include a first, proximal opening that is disposed adjacent to the port and a second, distal opening that is disposed adjacent to the end effector receiver. In some embodiments, the device can include three fluid seals. The first fluid seal can be disposed on and around the shaft, proximal of the first, proximal opening. The second seal can be disposed on and around the shaft, distal of the first, proximal opening. The third seal can be disposed on and around a distal portion of the shaft. In some embodiments, other shafts, e.g., inner and/or intermediate shafts, can be provided within the inner lumen of the shaft and can include features such as those described above, known to those skilled in the art, and/or otherwise provided for in the present disclosure.

In one exemplary embodiment of a surgical method, either a vacuum force or an irrigation force can be applied to a proximal compartment of a surgical device. The vacuum force is effective to move at least one of fluid and tissue from a distal compartment of the surgical device, through the proximal compartment, and out of a port that is in fluid communication with the proximal compartment. The irrigation force is effective to remove at least one of fluid and tissue from the distal compartment by applying fluid through the proximal compartment and to the distal compartment to move at least one of fluid and tissue through one or more openings formed in the distal compartment. The proximal compartment includes first and second fluid seals disposed on and around an outer shaft that is located within the proximal compartment of the surgical device, and the distal compartment includes a third seal disposed on and around the outer shaft located within the distal compartment of the surgical device. The first seal is disposed proximal of a proximal opening formed in the outer shaft such that fluid is prevented from flowing proximally out of the proximal compartment by passing directly adjacent to the first seal, while the second seal is disposed distal of the opening formed in the outer shaft such that fluid is prevented from flowing distally out of the proximal compartment by passing directly adjacent to the second seal. Further, the third seal is disposed on a portion of the outer shaft that is located within the distal compartment such that fluid is prevented from flowing proximally out of the distal compartment by passing directly adjacent to the third seal.

In some embodiments, the method can including applying the other of the vacuum force and the irrigation force to the proximal compartment of the surgical device. The vacuum force and/or the irrigation force can travel between the proximal compartment and the distal compartment by way of a lumen extending a length of an inner shaft that is disposed within the outer shaft. The method can also include advancing the inner shaft distally within the outer shaft to couple an end effector to the outer shaft.

BRIEF DESCRIPTION OF DRAWINGS

This disclosure will be more fully understood from the following detailed description taken in conjunction with the accompanying drawings, in which:

FIG. 1B is an isometric view of the surgical device of FIG. 1A;

FIG. 2A is a partially transparent, detailed isometric view of the port, first and second seals, proximal portions of the outer, intermediate, and inner shafts, and hub of FIG. 1C being in a locked or cleaning configuration, with the port being illustrated in a transparent manner;

FIG. 2B is a transparent detailed perspective view of the port of FIG. 2A;

FIG. 2C is a partially transparent, partial cross section side view of the port, first and second seals, proximal portions of the outer, intermediate, and inner shafts, and the hub, with the port being illustrated in a transparent manner and the hub being visible as a cross-section taken along line C-C shown in FIG. 1C;

DETAILED DESCRIPTION

Figure 1A:
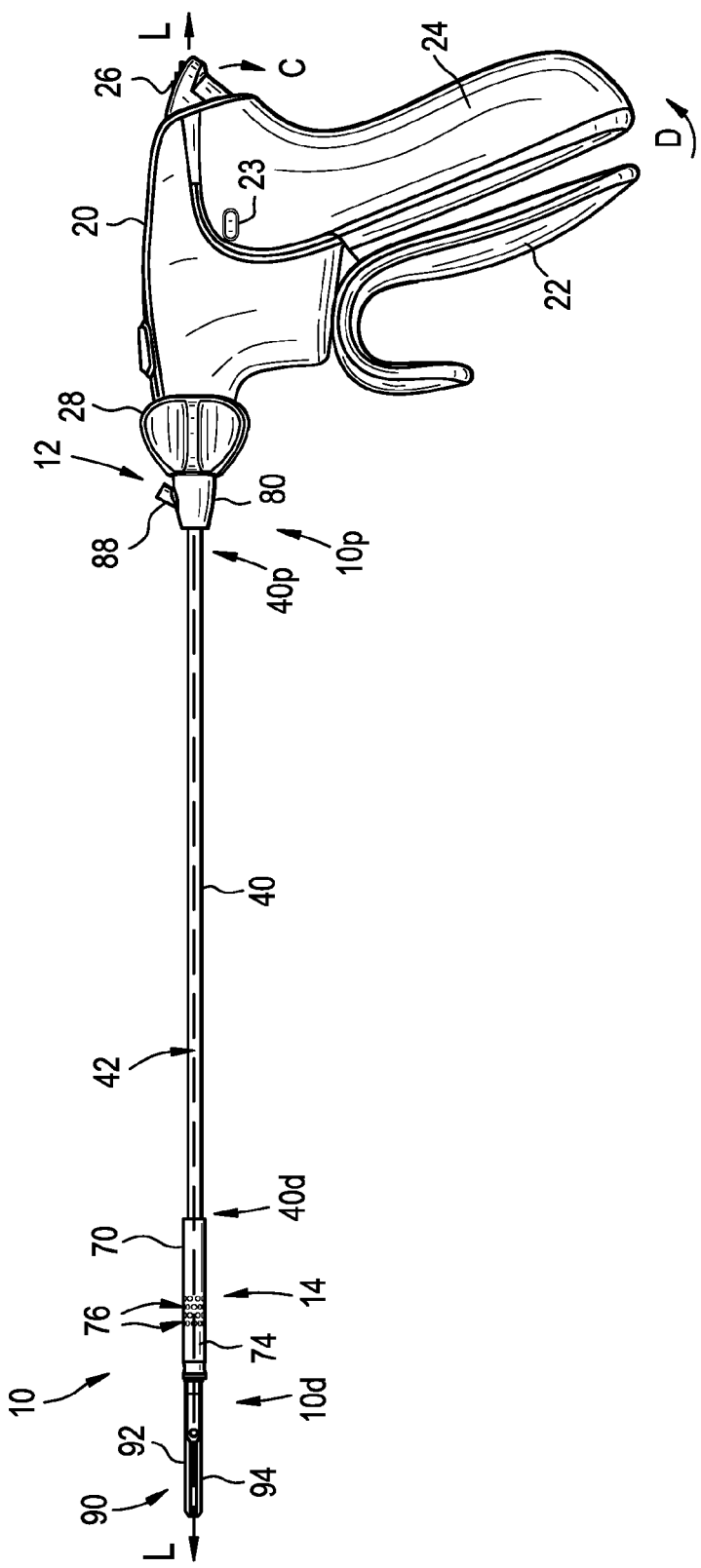
FIG. 1A is a side view of one exemplary embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Still further, a person skilled in the art will recognize that a number of different terms can be used interchangeably while still being understood by the skilled person. By way of non-limiting examples, the terms "compartment" and "chamber" and "suction" and "vacuum" are generally used interchangeably herein.

The present disclosure generally relates to devices and methods for cleaning a surgical device. More specifically, the disclosed devices provide the ability to apply a vacuum or suction force to a distal end of the device, while also providing for the ability to interchangeably apply an irrigation or fluid force to the distal end of the device. The vacuum force can draw fluid and/or tissue away from the distal end, towards the proximal end of the device, to remove it, while the irrigation force can drive fluid and tissue out of the distal end of the device. A plurality of seals are used to create the chambers or compartments in which the forces can be applied so that fluid or tissue, whether being driven out of the device or supplied as part of a vacuum or irrigation force, is contained within those chambers and not into areas of the device or surrounding environment where fluid and tissue can be undesirable, e.g., the housing or handle portion and/or portions of an elongate shaft extending from the housing or handle portion such that the fluid and tissue passes to the surrounding environment. Openings can be formed in the various components of the device to allow for fluid communication between the proximal and distal ends, and to allow for fluid and/or tissue to be removed from the device.

FIGS. 1A-1F show an exemplary instrument of device 10 that can supply both a vacuum and an irrigation force to its distal end 10*d* and/or to an end effector 90 coupled to its distal end 10*d*. The device 10 has a handle portion or housing 20, an outer elongate shaft 40 extending distally from the housing 20, and an end effector receiver 70 disposed on a distal end 40*d* of the shaft 40 for selectively receiving an end effector 90, as shown a jaw assembly having jaws 92, 94. As shown, the outer shaft 40 can extend from a distal, upper portion of the housing 20, along a central longitudinal axis L of the shaft 40 extending therethrough, and it can be removably and replaceably attached to operable components in the housing 20 that are known to those skilled in the art. A port 80 can be disposed on the shaft 40 and can be used in conjunction with applying a vacuum force and an irrigation force. Although described in greater detail below, the port 80 is generally in fluid communication with the end effector receiver 70 via a pathway formed within a lumen 42 extending through the elongate shaft 40 so that vacuum and irrigation forces applied to the port 80 are effective with respect to the end effector receiver 70. In an illustrated exemplary embodiment, the pathway is formed by openings and lumens formed in the outer shaft 40, an inner shaft 50, and an intermediate shaft 60. Further, leaking of fluid and/or tissue out of the pathway and into other components of the device 10 and/or the surrounding environment can be limited or altogether prevented by the use of seals 82, 84, 86, as described in greater detail below.

The pathway can begin in the port 80, which is illustrated transparently in FIGS. 2A, 2B, and 2C. The port 80 can be a generally conical housing 81 having a central or inner lumen 83 extending therethrough. The central lumen 83 can be generally cylindrical and shaped to receive the outer shaft 40 therein. As a result, the port 80, and its central lumen 83, can have a longitudinal axis $L_P$ that is coaxial with the longitudinal axis L of the outer shaft 40. As shown in FIG. 2B, recesses 83r can be formed as part of the lumen 83 to receive the first and second seals 82 and 84. The recesses 83r can be sized to form an interference fit with the seals 82, 84, and the seals 82, 84 can be sized to couple to the outer shaft 40, such that fluid is prevented from passing directly adjacent to the seal, whether around an outer surface of the seals 82, 84 between the seals 82, 84 and the recesses 83r, or around an inner surface of the seals 82, 84 between the seals 82, 84 and outer shaft 40.

The port 80 can include an outlet 88 having a relief channel 89 formed therein that is formed on or otherwise coupled to the housing 81 such that the channel 89 is in fluid communication with the central lumen 83. As shown, the outlet 88 (and thus the channel 89) extends at an oblique angle α with respect to the central lumen 83 (and thus the longitudinal axes L and $L_P$ of the elongate shaft 40 and the port 80, respectively), with a proximal end 89p of the channel 89 extending to an outside environment and a distal end 89d of the channel 89 being adjacent to the central lumen 83 to allow for fluid communication therebetween. A vacuum or fluid source can be coupled to or otherwise associated with the outlet 88 and/or the port 80 at or near the proximal end 89p of the channel 89 so that the source can supply the corresponding vacuum or irrigation force to the proximal end 89p and through the distally extending pathway. In some embodiments, a valve 85 can be associated with the port 80. The valve 85 can be disposed in the relief channel 89, or at the entry point between the channel 89 and the central lumen 83, e.g., at or proximate to the distal end 89d, to control the flow of fluid between the channel 89 and the rest of the distally extending pathway in either direction. Controlling the flow of fluid includes allowing fluid to flow towards the distal end of the device 10 when an irrigation force is applied and towards the proximal end of the device 10 when a vacuum force is applied. A person skilled in the art will recognize that the valve 85, and/or other valves, can be disposed at other locations along the pathway to also control the flow of fluid in either direction.

In the illustrated embodiment, the generally conical housing 81 tapers from a proximal end 80p to a distal end 80d, although the housing 81 can have a variety of other shapes and configurations based, at least in part, on the size and shape of the other components of the device 10 and the type of procedure being performed. As shown, the proximal end 80p is substantially flat and is configured to sit flush with a hub 38 that receives the outer and intermediate shafts 40, 60. The distal end 80d is also substantially flat in the illustrated embodiment.

The space that exists in the outlet 88 and the port 80 through which fluid can pass can be described as a proximal chamber or compartment 12, with the proximal compartment 12 being defined, at least in part, by the space that exists in the channel 89 and the inner lumen 83. The proximal compartment 12 can be further defined by the first and second seals 82, 84 and any space that extends between the two seals 82, 84, the port 80, and the outer shaft 40 disposed therein. The first seal 82 can seal the proximal compartment 12 from the housing 20 and the second seal 84 can seal the proximal compartment 12 from a distally extending portion of the outer shaft 40. The first seal 82 can thus prevent fluid from flowing proximally out of the proximal compartment 12, e.g., by passing directly adjacent to the first seal 82, and into components of or associated with the housing 20. Likewise, the second seal 84 can prevent fluid from flowing distally out of the proximal compartment 12, e.g., by passing directly adjacent to the second seal 84, and out of the device 10 entirely.

Figure 1C:
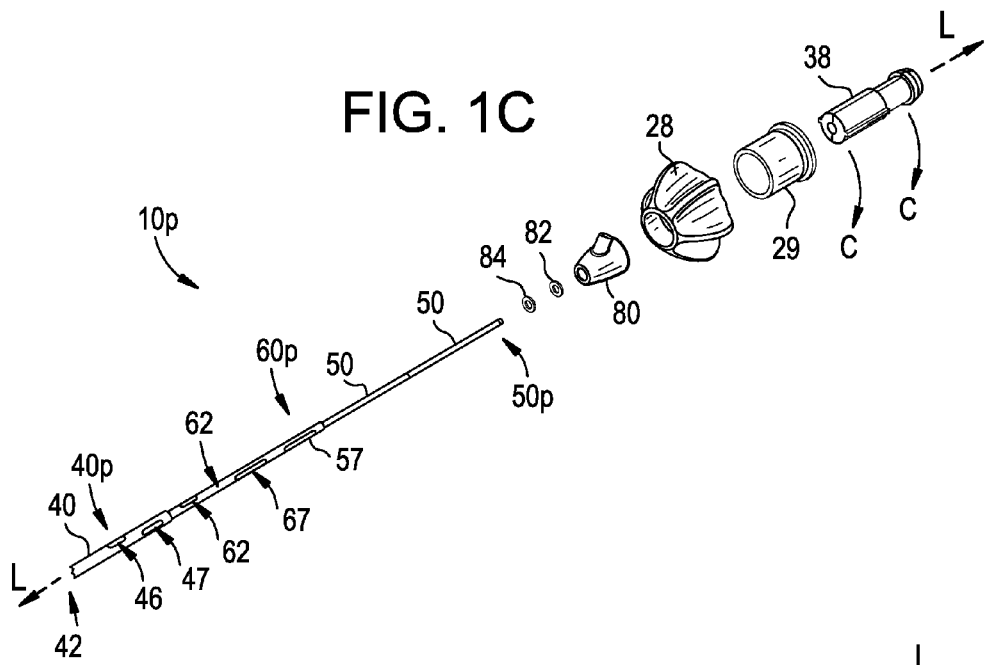
FIG. 1C is an isometric exploded view of portions of the surgical device of FIG. 1B, including a port, first and second seals, proximal portions of outer, intermediate, and inner shafts, and a hub.
Figure 1D:
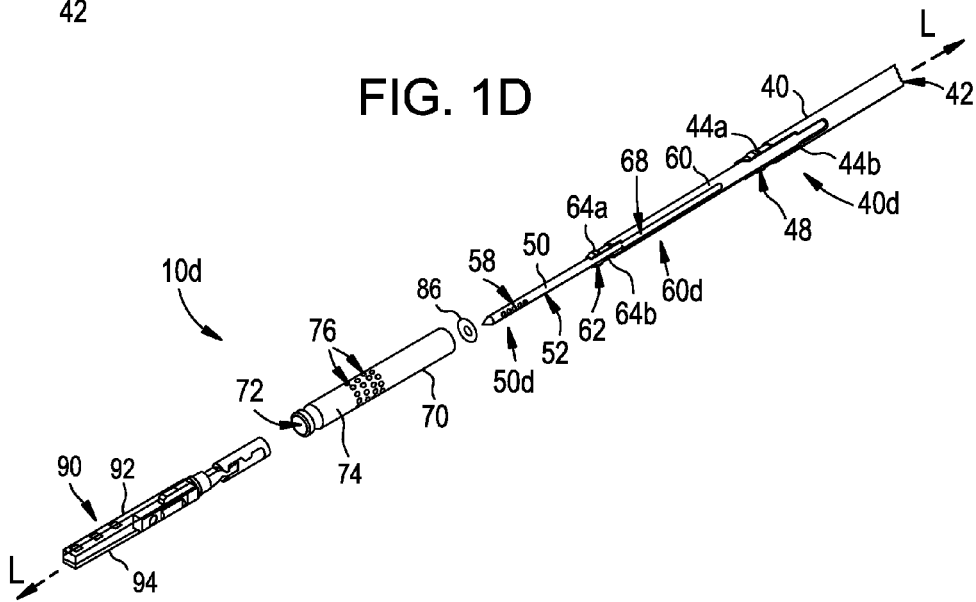
FIG. 1D is an isometric exploded view of portions of the surgical device of FIG. 1B, including an end effector, an end effector receiver, and distal portions of the outer, intermediate, and inner shafts of FIG. 1C.
Figure 1E:
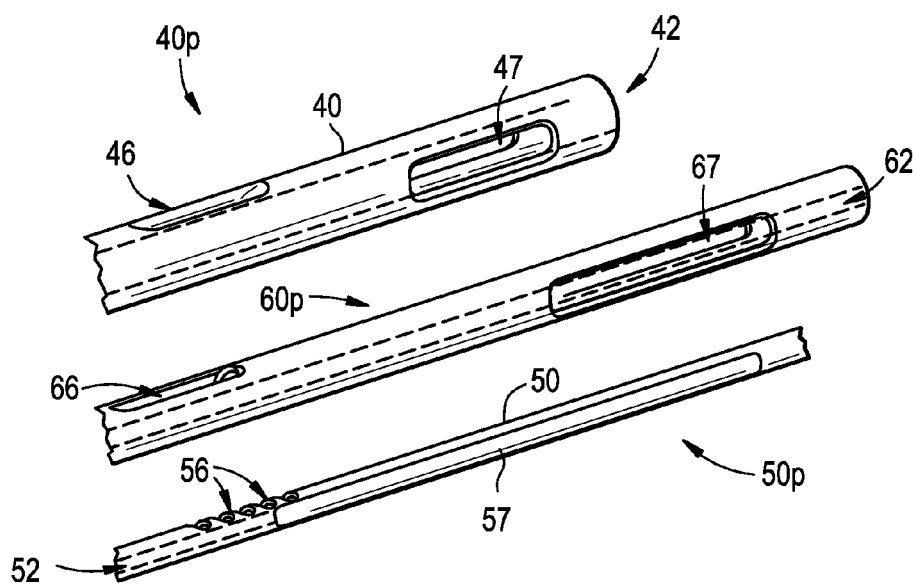
FIG. 1E is a perspective exploded view of proximal portions of the outer, intermediate, and inner shafts of FIG. 1C.
Figure 1F:
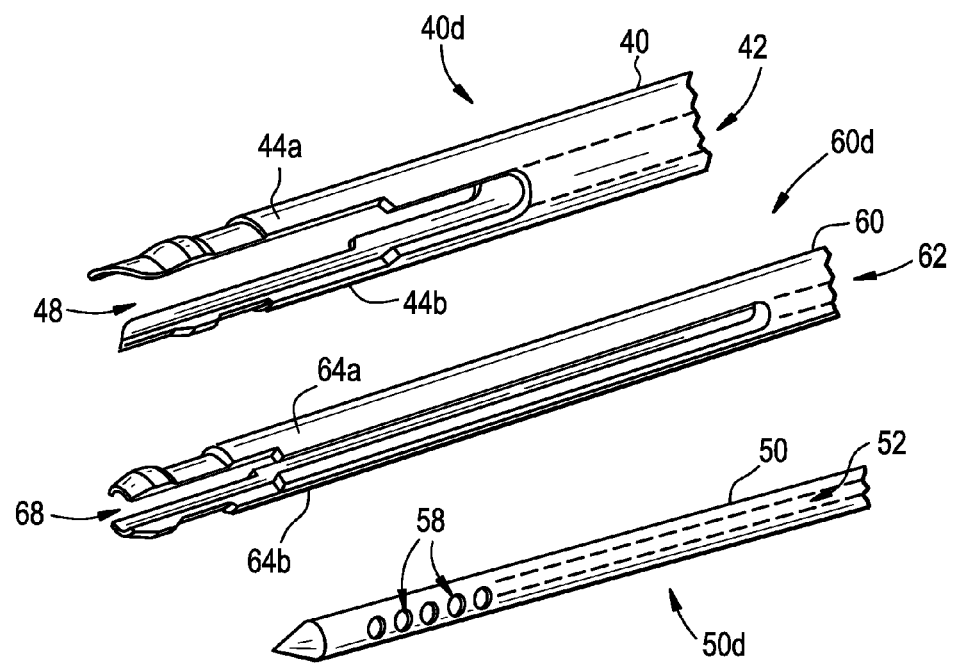
FIG. 1F is a perspective exploded view of distal portions of the outer, intermediate, and inner shafts of FIG. 1D.

The outer shaft 40 can be generally cylindrical and elongate with a lumen 42 defined by an inner sidewall, the lumen 42 extending from a proximal end 40p of the shaft 40 to the distal end 40d of the shaft 40. The proximal end 40p can be configured to be coupled to the housing 20, as shown by coupling to the hub 38 associated with the housing (FIG. 2C) such that the shaft 40 extends distally away from the housing 20. In some embodiments, the shaft 40 can be configured such that it can be removably and replaceably coupled to the housing 20, which allows the same shaft 40 to be cleaned and sterilized for reuse or for another shaft to be used in place of the shaft 40. As shown in FIGS. 1D and 1F, the distal end 40d of the shaft 40 includes opposed, deflectable arms 44a, 44b that are configured to deflect radially outward to engage a surface surrounding the distal end 40d to couple the shaft 40 to the surrounding surface, such as an inner surface of the end effector receiver 70, as described in greater detail below with respect to FIGS. 3A and 3B. As further shown, various surface contours can be formed on the arms 44a, 44b to assist with engaging the inner surface of the end effector receiver 70. The space extending between the deflectable arms 44a, 44b forms openings 48 of a distal portion 40d of the outer shaft 40.

Further, at least one opening 46 (best seen in FIG. 1E) is formed through a sidewall of a proximal portion 40p of the outer shaft 40, with the opening 46 being configured to be in fluid communication with the relief channel 89. In the illustrated embodiment, the opening 46 is substantially elliptical in shape and, when the outer shaft 40 is coupled to the housing 20 for operation, aligns with the distal end 89d of the channel 89, as shown in FIG. 2A. The opening 46 and the distal end 89d of the channel 89 also remain aligned in a cleaning or locked configuration, described in greater detail below. The shaft 40 can also include one or more alignment features to secure or at least restrict a location of the shaft 40 with respect to the housing 20. As shown, a second opening 47 is provided in the proximal portion 40p of the outer shaft 40, and helps align or otherwise secure a location of the outer shaft 40 with respect to the housing 20. This is accomplished, by way of non-limiting example, by the second opening 47 engaging a complementary post (not shown) of the hub 38 such that the outer shaft 40 does not rotate independently of the hub 38, and the length of the second opening 47 is such that an amount of axial travel (proximal-distal) by the outer shaft 40 is restricted by the ends of the second opening 47 engaging said complementary post. A person skilled in the art will recognize other alignment features that can also be used, and thus the outer shaft 40 is not limited to using the second opening 47, or openings in general, for alignment.

The inner shaft 50 can be generally cylindrical and elongate and can be coaxial with the outer shaft 40 such that they share a central longitudinal axis L. As designed, the inner shaft 50 is configured to translate along the central longitudinal axis L, through at least a portion of the outer shaft 40. The inner shaft 50 also includes a lumen 52 defined by an inner sidewall, the lumen 52 extending through a substantial length of the shaft 50. More particularly, in the illustrated embodiment, the lumen 52 extends from at least one opening 56 (best seen in FIGS. 1E and 2A) formed through a sidewall of a proximal portion of the inner shaft 60 to at least one opening 58 (best seen in FIG. 1F) formed through a sidewall of a distal portion of the inner shaft 60, thus allowing fluid communication between the two openings 56 and 58. In a cleaning or locked configuration in which a fluid or vacuum force is to be applied to the end effector receiver 70, the at least one opening 56 is aligned with the opening 46 of the elongate shaft 40 and the relief channel 89 to allow fluid communication from the channel 89, through the opening 46, through the opening 56, and through to the opening 58, which can be disposed within the end effector receiver 70. Fluid communication in the opposite direction is also possible in the cleaning or locked configuration.

In the illustrated embodiment, the at least one opening 56 and the at least one opening 58 are similarly shaped, and as shown each includes five generally circular openings disposed approximately equidistant from each other. The multiple, individual openings 58 as shaped can increase an amount of spread by the liquid that exits the lumen 52 of the inner shaft 50. In some embodiments, the openings 58 can be angled to allow for even further spread capabilities. The previously described pathway thus extends through the lumen 42 of the outer shaft 40 by way of the lumen 52 formed in the inner shaft 50, connecting the proximal compartment 12 that includes the port 80 to a distal compartment 14 that includes the end effector receiver 70. In some embodiments, a portion of the inner shaft 50 proximal of the openings 56 can include opposed channels 57 (only one of which is visible in FIGS. 1C, 1E, and 2C) formed in the sidewalls of the shaft 50. The shaft 50 can also include one or more alignment features to secure or at least restrict a location of the shaft with respect to the housing 20, the outer shaft 40, and/or the intermediate shaft 60. As shown, opposed channels 57 extend a portion of a length of the inner shaft 50 and help align or otherwise secure a location of the inner shaft 50 with respect to the housing 20. This is accomplished, by way of non-limiting example, by the channels 57 engaging one or more complementary protrusions formed in any of the intermediate shaft 60, the outer shaft 40, the hub 38, or a component disposed in and/or of the housing 20, such that the inner shaft 50 does not rotate independently of one or more of the intermediate shaft 60, the outer shaft 40, and the hub 38, as designed. A person skilled in the art will recognize other alignment features and configurations that can also be used, and thus the inner shaft 50 is not limited to using channels 57, or channels in general, for alignment.

In some embodiments, the inner shaft 50 can be used as an obturator, and thus its distal end 50d can have a pointed configuration that allows it to pierce tissue. In use, prior to coupling the shaft 40 to the end effector receiver 70, the distal end 50d of the inner shaft 50 can be extended distally beyond the distal end 40d of the shaft 40 to puncture tissue. A proximal end 50p of the shaft 50 can be configured to be coupled to the housing 20, for instance by coupling to one or more internal actuation components disposed within the housing 20 (not shown). The internal actuation components can then be operated to advance and retract the inner shaft 50, including placing it in the aforementioned cleaning configuration to allow fluid or tissue to move from one end of the pathway to the other. In the locked or cleaning configuration, the distal end 50d of the inner shaft 50 extends distally beyond the distal end 40d of the outer shaft 40. Further, advancing the inner shaft 50 distally can also couple the end effector receiver 70 to the outer shaft 40 (e.g., by causing the deflectable arms 48a, 48b to flex radially outward and engage an inner surface of the end effector receiver 70), as described in greater detail below with respect to the intermediate shaft 60.

The intermediate shaft 60 can also be generally cylindrical and elongate and can be coaxial with the outer and inner shafts 40, 50 such that they share a central longitudinal axis L. As designed, the intermediate shaft 60 is configured to translate along the central longitudinal axis L, through at least a portion of the outer shaft 40. The intermediate shaft 60 also includes a lumen 62 defined by an inner sidewall, the lumen 62 extending from a proximal end 60p of the shaft 60 to a distal end 60d of the shaft 60 so that the inner shaft 50 can be disposed within the intermediate shaft 60. The proximal end 60p can be configured to be coupled to the housing 20, for instance by coupling to one or more components disposed within the housing 20 (not shown). The internal actuation components can then be operated to advance and retract the intermediate shaft 60, including placing it in the aforementioned cleaning or locked configuration.

Figure 3A:
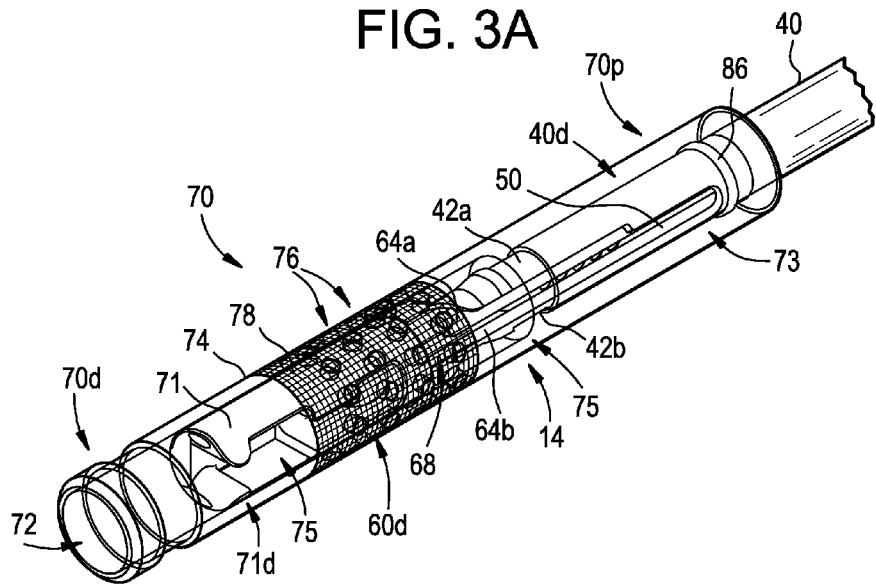
FIG. 3A is a partially transparent isometric view of the end effector receiver of FIG. 1D with the inner shaft advancing towards a locked or cleaning configuration.
Figure 3B:
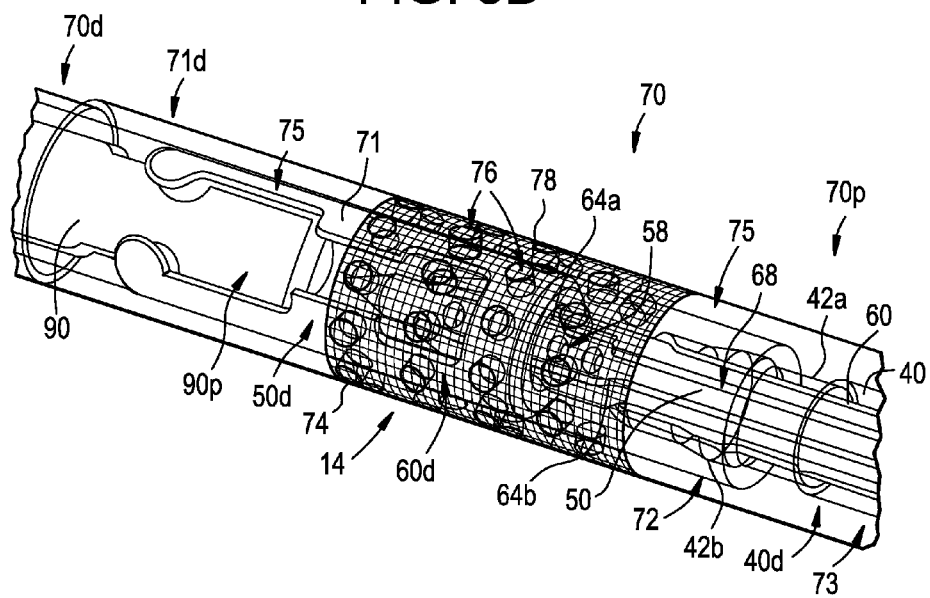
FIG. 3B is partially transparent detailed perspective view of the end effector receiver of FIG. 3A with the inner shaft, intermediate shaft, and the outer shaft being disposed in the locked or cleaning configuration.
Figure 4:
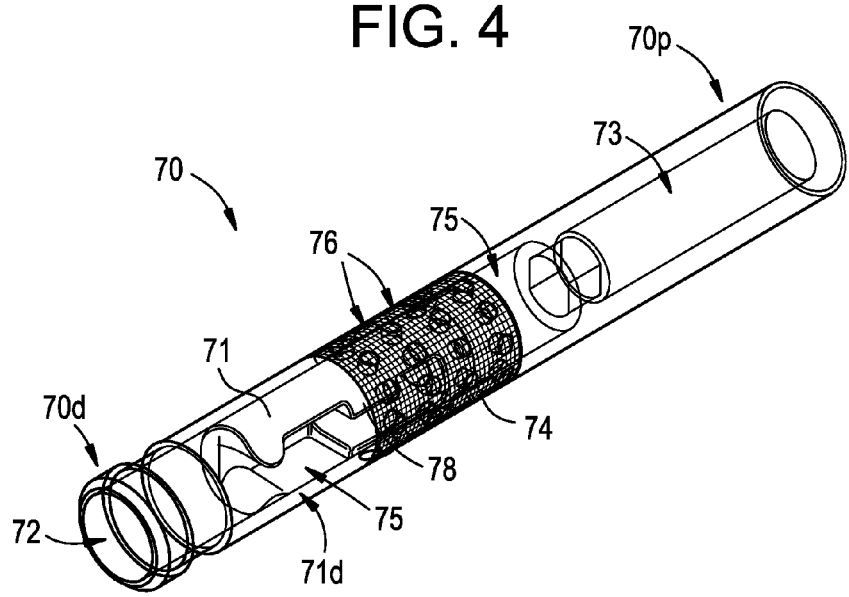
FIG. 4 is a partially transparent isometric view of the end effector receiver of FIG. 3A.

The distal end 60d can include opposed, deflectable arms 64a, 64b that are configured to deflect radially outward to engage a surface surrounding the distal end 60d to couple the shaft 60 to the surrounding surface, such as a coupler 71 of the end effector receiver 70, illustrated in FIGS. 3A, 3B, and 4. The space extending between the deflectable arms 64a, 64b forms openings 68 of a distal end 60d of the intermediate shaft 60. As the inner shaft 50 passes through the intermediate shaft 60 to move to the locked or cleaning configuration (provided for in FIGS. 2A and 3B), the deflectable arms 64a, 64b can be extended radially outward to engage a complementary coupling surface formed on an inner surface of the coupler 71. Likewise, as the arms 64a, 64b extend radially outward, they can cause the deflectable arms 44a, 44b of the outer shaft 40 to extend radially outward to engage a complementary coupling surface formed on an inner surface of the end effector receiver 70. As shown in FIG. 3B, when the device 10 is in the locked or cleaning configuration, the distal end 60d of the intermediate shaft 60 extends distally beyond the distal end 40d of the outer shaft 40, and the distal end 50d of the inner shaft 50 extends to or distally beyond the distal end 60d of the intermediate shaft 60. The result of the location of the shafts 40, 50, and 60, and the outward radially extension of the arms 44a, 44b and 64a, 64b as caused by the inner shaft 50 is that the end effector receiver 70, and thus an end effector 90 coupled thereto, is attached to the shaft 40, and as a result, the device 10. Accordingly, the end effector 90 can be operated by various features associated with the device 10, including those included as part of the housing 20.

Further, at least one opening 66 (best seen in FIG. 1E) is formed through a sidewall of a proximal portion of the intermediate shaft 60. As shown, the opening 66 is substantially elliptical in shape. In the aforementioned cleaning or locked configuration, the at least one opening 66 is aligned with the openings 56 of the inner shaft 50, the opening 46 of the elongate shaft 40, and the relief channel 89 to allow fluid communication from the channel 89, through the openings 46, 66, and 56, and through to the openings 58. Fluid communication in the opposite direction is also possible in the cleaning or locked configuration. The intermediate shaft 60 can also include one or more alignment features to secure or at least restrict a location of the shaft 60 with respect to the housing 20 or the outer shaft 40. As shown, a second opening 67 is provided in the proximal portion 60p of the intermediate shaft 60, and helps align or otherwise secure a location of the intermediate shaft 40 with respect to the housing 20 and/or the outer shaft 40. This is accomplished, by way of non-limiting example, by the second opening 67 engaging a complementary post of the hub 38 and/or the outer shaft 40 such that the intermediate shaft 60 does not rotate independently of the hub 38 or the outer shaft 40, and the length of the second opening 67 is such that an amount of axial travel (proximal-distal) by the intermediate shaft 60 is restricted by the ends of the second opening 67 engaging said complementary post. A person skilled in the art will recognize other alignment features that can also be used, and thus the intermediate shaft 60 is not limited to using the second opening 67, or openings in general, for alignment. Still further, while translating the inner shaft 50 through the outer shaft 40 can be effective to puncture tissue and/or couple an end effector receiver and/or an end effector to the outer shaft 40, translating the intermediate shaft 60 through the outer shaft 40 can be effective to actuate the end effector 90, as described in greater detail below.

As shown in FIG. 2C, the hub 38 can be configured to receive both the outer and the intermediate shafts 40 and 60. A lumen 39 of the hub 38 can have a proximal portion 39p with a diameter sized to be complementary to the intermediate shaft 60 and a distal portion 39d with a diameter sized to be complementary to the outer shaft 40. The proximal end 40p of the outer shaft 40 can terminate within the hub 38, while the intermediate shaft 60 and the inner shaft 50 can both extend through the hub 38 and into the housing 20 to be coupled to internal actuation components disposed in the housing 20. The translating movement of the intermediate and inner shafts 60 and 50 can be controlled by the internal actuation components, which themselves can be controlled by features of the housing 20 that are accessible to a user. For example, in the illustrated embodiment, a closure actuator 22 can be advanced towards a stationary arm 24, as illustrated in FIGS. 1A and 1B with the arrow D, to distally advance the intermediate shaft 60, and a locking member 26 can be rotated towards the housing 20, as illustrated in FIGS. 1A and 1B with the arrow C, to distally advance the inner shaft 50.

The internal actuation components that can be used to translate motion of components such as the closure actuator 22 and the locking member 26 can have many different configurations, including being mechanically, electrically, and/or optically-based, and components of this nature are known to those skilled in the art, thus exact details about every such component is unnecessary. Some non-limiting examples of such components are discussed in greater detail in U.S. application Ser. No. 14/836,069, filed on Aug. 26, 2015, and entitled "Surgical Device having Actuator Biasing and Locking Features," which is hereby incorporated by reference in its entirety. In general, such components can be disposed in, or attached to, portions of the housing 20 and/or the outer shaft 40. Some exemplary, non-limiting examples of these components include but are not limited to motors, controllers, and levers. Other implementations that can be used to advance and retract the shafts 50, 60 include but are not limited to actuator, gears, levers, triggers, and sliders. Further, a person skilled in the art will recognize other functions that the closure actuator 22 and the locking member 26, or other means of actuation, can perform without departing from the spirit of the present disclosure. Still further, some non-limiting examples of features that can be incorporated as part of the device 10 include a locking switch 23 to selectively lock the closure actuator 22 in a fixed angular position relative to the housing 20, and a knob 28 configured to rotate the elongate shaft 40, and thus an end effector 90 coupled thereto. Other non-limiting examples of actuation components include a rotation knob spring housing 29, as shown in FIG. 1C, which helps house a spring (not shown) that works with the knob 28, as would be understood by a person having skill in the art.

The end effector receiver 70 is configured to be removably and replaceably coupled to the distal end 40d of the elongate outer shaft 40 to couple an end effector, e.g., the end effector 90, to the device 10. As shown, the end effector receiver 70 is generally cylindrical in shape and includes a lumen 72 defined by an inner sidewall, the lumen 72 extending from its proximal end 70p to its distal end 70d. The lumen 72 has multiple diameters and a non-uniform shape across its length such that the shape of the lumen 72 defined by an inner sidewall of the end effector receiver 70 can be complementary at least to the configuration of the distal end 40d of the outer shaft 40. Further, disposed in the end effector receiver 70 is a coupler 71 that has a geometry at its proximal end 71p that is complementary in shape to the geometry of the distal end 60d of the intermediate shaft 60. As a result, when the inner shaft 50 expands the arms 42a, 42b of the inner shaft 40 and the arms 62a, 62b of the intermediate shaft 60, the arms 42a, 42b and 62a, 62b form an interference fit with the complementary shape of the inner walls of the end effector receiver 70 and the coupler 71 that define their openings 73, 75, respectively.

A distal end 71d of the coupler 71 can be configured to receive an end effector, e.g., the end effector 90, and the shape of the inner wall that defines the opening 75 at the distal end 71d can be complementary to the shape of a proximal end 90p of the end effector 90. Distal advancement of the intermediate shaft 60 can then be effective to actuate the end effector 90, as known to those skilled in the art. This can occur, for example, by the distal end 60d contacting the proximal end 90p to initiate actuation, or by distal advancement of the intermediate shaft 60 also causing distal advancement of the inner shaft 50, which in turn causes the distal end 50d to contact the proximal end 90p to initiate actuation.

An outer wall 74 of the end effector receiver 70 can have one or more openings or blow-out ports 76 formed therein, the openings 76 extending from the outer wall 74 and into the inner lumen 72 such that the openings 76 are in fluid communication with the inner lumen 72. In the illustrated embodiment, a plurality of openings 76 extend around an entire circumference of the end effector receiver 70 (i.e., 360 degrees), and a plurality of rows are formed along the length of the end effector receiver 70, as illustrated four rows. The openings 76 can serve as an outlet through which fluid can be passed from the inner lumen 72 and out of the openings 76 to an outside environment. Tissue or other objects, if they are small enough, can also be passed through the openings 76.

In some embodiments, the openings 76 can have one or more screens associated with them. In the illustrated embodiment, a single screen 78 is disposed around the circumference of the sidewall that defines the inner lumen 72 such that the screen 78 covers each of the openings 76. In another embodiment, a second screen (not shown because difficult to illustrate and show the other features of the present disclosure) is also disposed around the circumference of the sidewall that defines the inner lumen 72 such that it too covers each of the openings 76. The two screens can be offset with respect to each other, e.g., oriented 90 degrees to one another, and spaced a distance apart from each other, e.g., approximately 0.003 millimeters from each other. As a result, openings in the first screen 78 are partially aligned with openings in the second screen. Using the screen 78, and/or using a second screen with the screen 78, can allow fluid to pass therethrough and capture tissue, which can prevent the openings 76 from being clogged. A person skilled in the art will recognize a variety of other configurations of screens are possible, including but not limited to two screens being offset at other orientations with respect to each other (e.g., oriented 45 degrees to one another), being spaced apart different distances, having more than two screens, and/or having a screen(s) disposed individually over or within the openings 76, including having two offset screens spaced a distance apart from each other disposed over or within single openings 76.

The distal chamber or compartment 14 can be defined, at least in part, by the space that exists within the end effector receiver 70, and can be further defined by a third seal 86 sealing the distal compartment 14 from a proximally extending portion of the outer shaft 40, as shown in FIG. 3A. Thus, the third seal 86 can prevent fluid from flowing proximally out of the distal compartment 14, e.g., by passing directly adjacent to the third seal 86, and out of the device 10 entirely. In the illustrated embodiment, the third seal 86 is disposed proximally of the openings 48 and 68 so that an inner surface of the seal 86 can be entirely in contact with an outer surface of the outer shaft 40 so that a seal can be maintained between the seal 86 and the outer shaft 40. A person skilled in the art will recognize other locations for the seal or other configurations that can also create the desired seal for the distal compartment 14. Further, similar to the central lumen 83 of the port 80, the inner lumen 72 can include a recess formed therein to receive the third seal 86 and form a similar interference fit between the third seal 86 and the recess, with the third seal 86 also coupling to the outer shaft 40 (and in some instances portions of the intermediate shaft 60 and/or the inner shaft 50), thereby preventing fluid from passing directly adjacent to the seal, whether around an outer surface of the seal 86 between the seal 86 and the recess, or around an inner surface of the seal 86 between the seal 86 and the outer shaft 40.

Fluid passes into the distal compartment 14 from the proximal compartment 12 and through the pathway via the openings 58 formed in the inner shaft 50. As shown in FIG. 3B, the distal end 50d of the shaft can be disposed within the distal compartment 14 in the cleaning or locked configuration, and thus fluid flowing through the lumen 52 can pass out of the openings 58, through the openings 68 in the intermediate shaft, and into the inner lumen 72. Fluid and tissue can also be passed in the reverse direction, from the distal compartment 14, through the openings 58 and the lumen 52, and out of the relief channel 89 in the port 80. As shown, the openings 48 of the outer shaft 40 do not extend to the location where the openings 58 are, although in other embodiments or configurations fluid can also pass through the openings 48 of the outer shaft 40.

Figure 5:
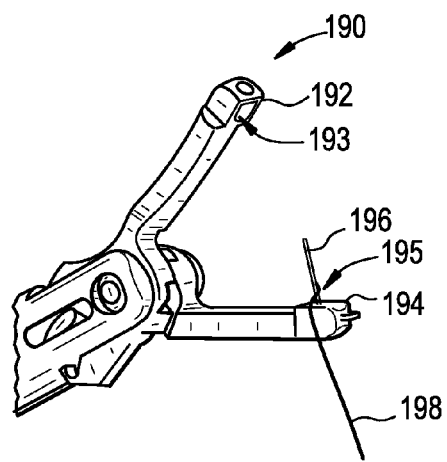
FIG. 5 is a perspective view of one exemplary embodiment of an end effector that is a suturing head.

While the end effector 90 illustrated in FIGS. 1A-3B is a jaw assembly, any number of end effectors can be used in conjunction with the device 10 provided for in the present disclosure. By way of non-limiting example, FIG. 5 illustrates one exemplary embodiment of a suturing head 190 that can be used as an end effector. As known by those having skill in the art, a suturing head is used to assist with suturing tissue in vivo. Because suturing heads are generally known to those skilled in the art, a detailed explanation as to how they work is unnecessary. As a basic overview, generally a needle 196 having suture 198 attached to it is passed between two jaws 192 and 194, with the jaws 192, 194 being configured to intermittingly release and receive the needle 196 using techniques known to those skilled in the art and/or provided for in the present disclosure below. As shown, the jaws 192 and 194 include openings 193 and 195, respectively, capable of alternating between holding and releasing the needle 196. Tissue can be disposed between the jaws 192, 194 so that as the needle 196 is passed from one jaw 192 to the other, the needle 196 threads the suture 198 into the tissue.

Figure 6A:
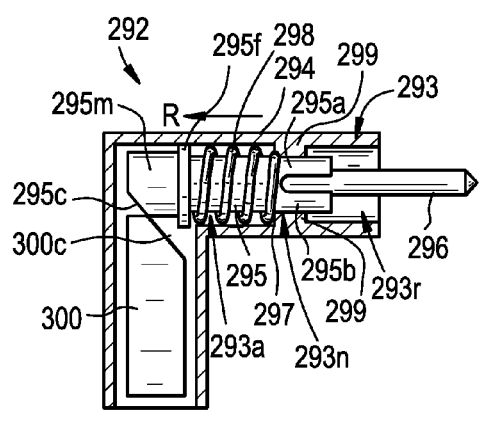
FIG. 6A is a cross-sectional view of an exemplary embodiment of a jaw for use as part of a suturing head, the jaw having a collet holding a needle.
Figure 6B:
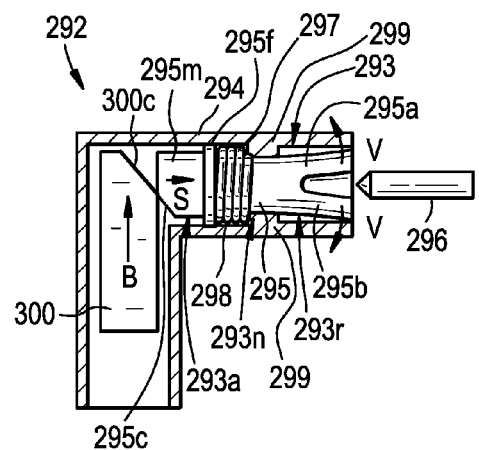
FIG. 6B is a cross-sectional view of the jaw of FIG. 6A, the needle being released from the collet.

FIGS. 6A and 6B and FIGS. 7A and 7B provide two illustrations of a jaw 292, 292' configured to both hold and release a needle in conjunction with being used in a suturing head. As shown in FIGS. 6A and 6B, the jaw 292 can include a housing 294 having an opening 293 formed therein with a collet 295 disposed in the opening 293. The opening 293 can have multiple diameters, with a receiving opening 293r and an actuator opening 293a having a neck opening 293n disposed therebetween. The collet 295 can include opposed deflectable arms 295a, 295b disposed at a distal end 295d of the collet 295 and are configured to receive and release the needle 296. In particular, in the illustrated embodiment, the arms 295a, 295b are configured to be biased radially outward. The collet 295 can also include a proximal base 295m at its proximal end 295p, the base 295b also including a flange 295f. A spring 298 can be disposed between the flange 295f and a ledge 297 formed as a result of the diameter of the neck opening 293n being smaller than the diameter of the actuator opening 293a. The spring 298 can be biased such that it deflects the flange 295 in a direction R, which results in the arms 295a, 295b of the collet 295 being biased radially inward by walls or camming slots 299 that form the neck opening 293n. As shown in FIG. 6A, when the arms 295a, 295b are biased radially inward by the walls 299, the needle 296 can be held by the arms 295a, 295b. Thus, in use, when the needle 296 is in the jaw 292 to pass suture attached to the needle 296 through the tissue, the collet 295 is biased in the direction R to hold the needle 296 within the collet arms 295a, 295b, and thus the jaw 292.

The needle 296 can be released from the jaw 292 by operating an actuator 300 disposed in the jaw 292 to operate against the bias of the spring 298. As shown in FIG. 6B, as the actuator 300 is pushed in a direction B, it contacts the base 295b of the collet 295 and drives the collet 295 in the direction S, which is opposite to the direction R and against the bias of the spring 298. Driving the collet 295 in the direction S causes the arms 295a, 295b to pass out of the walls 299, and thus, because the arms 295a, 295b are configured to be biased radially outward, the arms move in the direction V as shown. As a result, the arms 295a, 295b disengage the needle 296, allowing the needle 296 to be removed from the jaw 292 and passed to an opposed jaw or removed for cleaning purposes.

As shown, the actuator 300 includes a chamfered edge 300c that is complementary to a chamfer 295c formed in the base 295b of the collet 295. The chambered edges 300c and 295c engage each other when the actuator 300 drives the collet 295 in the direction S. A person skilled in the art will recognize a variety of other configurations that can be used to move the collet 295 between a position in which it grips the needle 296, as shown in FIG. 6A, and a position in which it releases the needle 296, as shown in FIG. 6B, whether using an actuator 300 or other mechanism to control movement of the collet 295. Movement of the actuator 300 can likewise be achieved using a variety of techniques known to those skilled in the art. For instance, by way of non-limiting example, in embodiments in which a suturing head having the jaw 292 is disposed at a distal end of the device 100, the closure actuator 22 can be operated to advance and retract the intermediate shaft 60, which in turn advances and retracts the actuator 300.

Figure 7A:
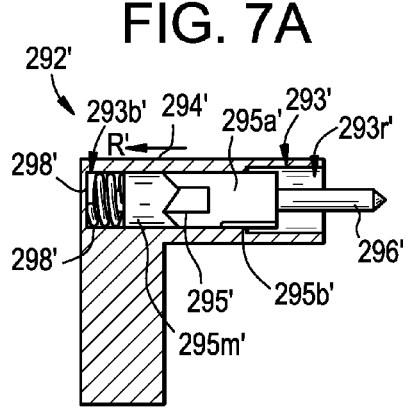
FIG. 7A is a cross-sectional view of another exemplary embodiment of a jaw for use as part of a suturing head, the jaw having a collet holding a needle.
Figure 7B:
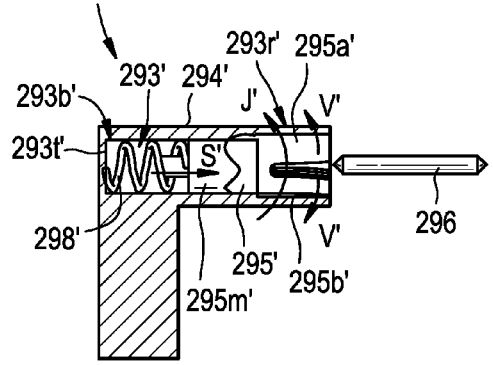
FIG. 7B is a cross-sectional view of the jaw of FIG. 7A, the needle being released from the collet.

FIGS. 7A and 7B provide an alternative embodiment of a jaw 292' configured to both hold and release a needle 296' in conjunction with being used in a suturing head. As shown, the jaw 292' can include a housing 294' having an opening 293' formed therein with a collet 295' disposed in the opening 293'. The opening 293' can have multiple diameters, with a receiving opening 293r' having a larger diameter than a base opening 293b'. The collet 295' can include opposed deflectable arms 295a', 295b' disposed at a distal end 295' of the collet 295' and are configured to receive and release a needle 296'. In particular, in the illustrated embodiment, the arms 295a', 295b' are configured to be biased radially outward. The collet 295' can also include a proximal base 295m' at its proximal end 295p'. A spring 298' can be disposed between the base 295b' and a terminal wall 293t' of the opening 293', with the spring 298' being biased such that it pulls the base 295b' of the collet 295' towards the terminal wall 293t' in a direction R'. This results in the arms 295a', 295b' of the collet 295' being biased radially inward by walls or camming slots 299' that form the base opening 293b'. As shown in FIG. 7A, when the arms 295a', 295b' are biased radially inward by the walls 299', the needle 296' can be held by the arms 295a', 295b'. Thus, in use, when the needle 296' is in the jaw 292' to pass suture attached to the needle 296' through the tissue, the collet 295' is biased in the direction R' to hold the needle 296' within the collet arms 295a', 295b', and thus the jaw 292'.

The needle 296' can be released from the jaw 292' in a variety of manners. In one exemplary embodiment, a jaw (not shown) opposed to the jaw 292' can push against the jaw 292' to cause the collet 295' to travel in the direction S', which is opposite to the direction R' and against the bias of the spring 298'. Driving the collet 295' in the direction S' causes the arms 295a', 295b' to pass out of the walls 299' and rotate in a direction J', and thus, because the arms 295a', 295b' are configured to be biased radially outward, the arms move in the direction V' as they rotate in the direction J' as shown. As a result, the arms 295a', 295b' disengage the needle 296', thus allowing the needle 296' to be removed from the jaw 292' and passed to an opposed jaw or removed for cleaning purposes. A person skilled in the art will recognize a variety of other configurations that can be used to move the collet 295' between a position in which it grips the needle 296', as shown in FIG. 7A, and a position in which it releases the needle 296', as shown in FIG. 7B, whether using an opposed jaw or other mechanism to control movement of the collet 295'. Movement of an opposed jaw or other actuator can likewise be achieved using a variety of techniques known to those skilled in the art. For instance, by way of non-limiting example, in embodiments in which a suturing head having the jaw 292' is disposed at a distal end of the device 100, the closure actuator 22 can be operated to advance and retract the intermediate shaft 60, which in turn advances and retracts the collet 295'.

A person skilled in the art will recognize other types of suturing heads with which the present disclosures can be used, including the surgical suturing device disclosed in U.S. Published Application No. 2014/0171972, entitled "Circular Needle Applier with Offset Needle and Carrier Tracks," filed Mar. 15, 2013, the suture needle driving instrument disclosed in U.S. Pat. No. 8,906,043, entitled "Laparoscopic Suturing Instrument with Perpendicular Eccentric Needle Motion," filed Nov. 14, 2011, and issued Dec. 9, 2014, and U.S. Pat. No. 9,113,861, entitled "Articulating Needle Driver," filed May 8, 2012, and issued Aug. 25, 2015, the contents of each which is hereby incorporated by reference in its entirety. Likewise, a person skilled in the art will recognize other non-limiting types of end effectors that can be used in conjunction with the present disclosures to provide easy cleaning of such end effectors and improving the ability to reuse devices, including radio frequency bipolar jaws, such as those disclosed in U.S. Ser. No. 14/166,133, entitled "Improved Motor Control and Feedback in Powered Surgical Devices," filed Jan. 28, 2014, monopolar hook, and monopolar handle attachments, such as those disclosed in U.S. Ser. No. 14/547,882, entitled "Energy Delivery Device Having a Translating Outer Sheath," filed Nov. 19, 2014, the contents of both of which are incorporated herein by reference in their entireties. Further, the end effectors can be used interchangeably with the device 10, as end effectors can be easily coupled to and released from the coupler 72 of the end effector receiver 70, or other configurations otherwise known or derivable from the present disclosure for associating an end effector with a surgical device.

A person skilled in the art will recognize the typical shapes and sizes of the various components of the device 10, and components associated with the device 10, e.g., the end effector 90, the suturing head 190, and the jaws 292, 292'. The shapes and sizes of the components can depend, at least in part, on the shape and size of the other components, the type of procedure being performed, and the preferences of the user. Likewise, a person skilled in the art will recognize the types of materials that can be used to form the various components of the device 10, and components associated with the device. By way of non-limiting examples, the shafts, end effectors, and jaws of an end effector and/or a suturing head can be made from surgical grade stainless steel (e.g., 17-4), other 300 and 400 series stainless steels, titanium, and aluminum, the housing of the handle portion can be made from a polymer (e.g., polycarbonate), and components disposed in the handle portion, e.g., motors, controllers, levers, etc., can be made from various materials typically used to form such components.

In use, the surgical device 10 can be placed into a cleaning or locked configuration (illustrated at least in FIGS. 2A and 3B) to allow a vacuum force and/or an irrigation force to be supplied to the distal end 10d of the device 10 and/or the end effector 90 to clean it. For example when the end effector 90 is a suturing head that includes the jaws 292, 292', after the needle 296, 296' has been passed at least once from one jaw to another, the closure actuator 22 of the handle portion 20 can be pressed towards the stationary arm 24 in the direction D and the locking member 26 can be depressed towards the housing in the direction C to advance the intermediate and inner shafts 60, 50, respectively, distally into the cleaning or locked configuration illustrated in FIG. 3B. In the cleaning or locked configuration, the openings 46, 66, and 56 in the outer, intermediate, and inner shafts 40, 60, and 50 are aligned with the relief channel 89 as shown in FIG. 2A to allow fluid communication from the channel 89 and into the inner lumen 52 of the inner shaft 50. Likewise, the openings 58 and 68 in the inner and intermediate shafts 50 and 60 are disposed in the end effector receiver 70 as shown in FIG. 3B to allow fluid communication from the inner lumen 52 of the inner shaft 50 with the inner lumen 72 of the end effector receiver 70, as well as the openings 76 formed in the outer wall 74 of the end effector receiver 70.

Once in the cleaning or locked configuration, a vacuum source or an irrigation source can be coupled to the device 10 to supply a respective vacuum force or an irrigation force to the proximal end of the channel. The vacuum source can suck fluid and tissue from the distal compartment 14, i.e., the end effector receiver 70, and/or the end effector 90, through the openings 68 and 58 of the intermediate and inner shafts 60 and 50, through the lumen 52 of the inner shaft 50, through the openings 56, 66, and 46 of the inner, intermediate, and outer shafts 50, 60 and 40, and out of the proximal compartment 12, i.e., the inner lumen 83 of the port 80 and the relief channel 89. As a result, fluid and tissue is removed from the distal end 10d of the device 10.

Likewise, the irrigation source can supply water or other fluid from the proximal compartment 12, i.e., the relief channel 89 and the inner lumen 83 of the port 80, through the openings 46, 66, and 56 of the outer, intermediate, and inner shafts 40, 60, and 50, through the lumen 52 of the inner shaft 50, through the openings 58 and 68 of the inner and intermediate shafts 50 and 60, and to the distal compartment 14, i.e., the end effector receiver 70, and/or the end effector 90. As a result, the fluid can drive other fluid and tissue out of the distal end 10d of the device 10 through the openings 76 of the end effector receiver 70. The seals 82, 84, and 86 formed in the proximal and distal compartments 12 and 14 can help prevent fluid from flowing out of the compartments 12 and 14, thereby minimizing undesirable leaking of fluid into the housing 20, the device more generally, and/or the environment surrounding the device 10.

A user can selectively apply vacuum and irrigation forces to achieve various goals in cleaning. For example, a user may first supply an irrigation force to drive some material, e.g., fluid and tissue, out of the openings 76, and then afterward supply a vacuum force to remove any remnants located in the end effector receiver 70. Multiple vacuum or irrigation forces can also be supplied, depending, at least in part, on the desired outcome of the cleaning being performed and the types of materials being removed from the end effector receiver 70 and/or the end effector 90.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. By way of non-limiting example, although the present disclosure describes embodiments that utilize three shafts—outer, intermediate, and inner shafts—in other embodiments fewer shafts may be used such that the vacuum and irrigation forces can be supplied through only one or two shafts. All publications and references cited herein are expressly incorporated herein by reference in their entirety.

What is claimed is:

1. A surgical device, comprising:
    a housing;
    an outer shaft coupled to the housing and extending distally therefrom, the outer shaft having a sidewall, a proximal portion, a distal portion, and an inner lumen extending between the proximal and distal portions, each of the proximal and distal portions having at least one opening formed in the sidewall;
    a port coupled to the proximal portion of the outer shaft, the port having a relief channel formed therein, the relief channel having a valve associated therewith and the relief channel being in fluid communication with the at least one opening formed in the sidewall of the proximal portion of the outer shaft;
    an end effector receiver removably coupled to the distal portion of the outer shaft, the end effector receiver having a sidewall with one or more openings formed therein and an inner lumen, the inner lumen being in fluid communication with the inner lumen of the outer shaft;
    a first fluid seal disposed on and around the outer shaft and disposed proximal of the at least one opening formed in the sidewall of the proximal portion of the outer shaft;
    a second fluid seal disposed on and around the outer shaft and disposed distal of the at least one opening formed in the sidewall of the proximal portion of the outer shaft; and
    a third fluid seal disposed on and around the distal portion of the outer shaft.

2. The surgical device of claim 1, further comprising:
    an inner shaft disposed within the inner lumen of the outer shaft and configured to translate relative to the outer shaft along a longitudinal axis thereof, the inner shaft having a sidewall, a proximal portion, a distal portion, and an inner lumen extending between the proximal and distal portions, each of the proximal and distal portions having at least one opening formed in the sidewall, the inner shaft being configured such that, in a locked configuration, the at least one opening formed in the sidewall of the proximal portion of the inner shaft is in fluid communication with the at least one opening formed in the sidewall of the proximal portion of the outer shaft, and the at least one opening formed in the sidewall of the distal portion of the inner shaft is in fluid communication with inner lumen of the end effector receiver.

3. The surgical device of claim 2, wherein the end effector receiver is configured to be decoupled from the outer shaft when the device is in an unlocked configuration.

4. The surgical device of claim 2, further comprising:
an intermediate shaft disposed between the outer shaft and the inner shaft, the intermediate shaft having a sidewall, a proximal portion, a distal portion, and an inner lumen extending between the proximal and distal portions, each of the proximal and distal portions having at least one opening formed in the sidewall, the intermediate shaft being configured to translate relative to the outer shaft along the longitudinal axis thereof,
wherein, in the locked configuration, a distal end of the inner shaft is disposed at or distal of a distal end of the intermediate shaft and the distal end of the intermediate shaft is disposed distal of a distal end of the outer shaft, with the at least one opening formed in the sidewall of the proximal portion of the intermediate shaft being in fluid communication with the at least one openings formed in the sidewalls of the proximal portions of the outer shaft and the inner shaft, and the at least one opening formed in the sidewall of the distal portion of the intermediate shaft being in fluid communication with the at least one opening formed in the sidewall of the distal portion of the inner shaft and the inner lumen of the end effector receiver.

5. The surgical device of claim 4, wherein the end effector receiver further comprises a coupler disposed within the inner lumen of the end effector receiver, the coupler having a proximal portion coupled to the intermediate shaft in the locked configuration and a distal portion configured to receive an end effector such that the end effector is operable by one or more components of the housing when coupled to the distal portion of the coupler.

6. The surgical device of claim 1, further comprising a screen disposed over or in the one or more openings formed in the sidewall of the end effector receiver.

7. The surgical device of claim 6, wherein the screen comprises a first screen and a second screen offset with respect to each other such that openings in the first screen are partially aligned with openings in the second screen.

8. The surgical device of claim 7, wherein the first and second screens are spaced a distance radially apart from each other.

9. The surgical device of claim 1, wherein the first and second fluid seals are disposed within the port.

10. The surgical device of claim 1, wherein the relief channel is disposed at an oblique angle with respect to the outer shaft, with an end of the channel disposed adjacent to the at least one opening formed in the sidewall of the proximal portion of the outer shaft being more distal than an opposed end of the channel disposed radially outward from the outer shaft.

11. The surgical device of claim 1, further comprising a suturing head coupled to the end effector receiver.

12. A surgical device, comprising:
a housing;
a shaft coupled to the housing and extending distally therefrom, the shaft having a sidewall, an inner lumen, and at least one opening formed in the sidewall such that the at least one opening is in fluid communication with the inner lumen;
an end effector receiver coupled to the shaft, distal of the housing, the end effector receiver having a sidewall with one or more openings formed therein and an inner lumen, the inner lumen being in fluid communication with the at least one opening formed in the sidewall of the shaft;
a screen disposed over or in the one or more openings formed in the sidewall of the end effector receiver; and
a port coupled to the shaft, the port having a relief channel formed therein that is in fluid communication with the at least one opening formed in the sidewall of the shaft, the port being configured to be operated in a first configuration in which a vacuum force is applied to the end effector receiver to move at least one of fluid and tissue from the end effector receiver to and out the relief channel of the port, and a second configuration in which a fluid is passed from the relief channel of the port to the end effector receiver to advance at least one of fluid and tissue disposed within the end effector receiver out of the one or more openings formed in the sidewall of the end effector receiver.

13. The surgical device of claim 12, wherein the screen comprises a first screen and a second screen offset with respect to each other such that openings in the first screen are partially aligned with openings in the second screen.

14. The surgical device of claim 13, wherein the first and second screens are spaced a distance radially apart from each other.

15. The surgical device of claim 12, wherein the at least one opening formed in the sidewall of the shaft comprises a first, proximal opening and a second, distal opening, the first, proximal opening being disposed adjacent to the port and the second, distal opening being disposed adjacent to the end effector receiver, the device further comprising:
a first fluid seal disposed on and around the shaft and disposed proximal of the first, proximal opening;
a second fluid seal disposed on and around the shaft and disposed distal of the first, proximal opening; and
a third fluid seal disposed on and around a distal portion of the shaft.

16. A surgical method, comprising:
applying one of a vacuum force and an irrigation force to a proximal compartment of a surgical device, the vacuum force being effective to move at least one of fluid and tissue from a distal compartment of the surgical device, through the proximal compartment, and out of a port in fluid communication with the proximal compartment, and the irrigation force being effective to remove at least one of fluid and tissue from the distal compartment by applying fluid through the proximal compartment and to the distal compartment to move at least one of fluid and tissue through one or more openings formed in the distal compartment,
wherein, the proximal compartment includes first and second fluid seals disposed on and around an outer shaft located within the proximal compartment of the surgical device, the first fluid seal being disposed proximal of a proximal opening formed in the outer shaft such that fluid is prevented from flowing proximally out of the proximal compartment by passing directly adjacent to the first seal, and the second seal being disposed distal of the opening formed in the outer shaft such that fluid is prevented from flowing distally out of the proximal compartment by passing directly adjacent to the second seal, and wherein the distal compartment includes a third seal disposed on and around the outer shaft, the outer shaft being located within the distal compartment of the surgical device, and the third seal being disposed on a portion of the outer shaft that is located within the distal compartment such that fluid is prevented from flowing proximally out of the distal compartment by passing directly adjacent to the third seal.

17. The method of claim 16, further comprising applying the other of the vacuum force and the irrigation force to the proximal compartment of the surgical device.

18. The method of claim 16, wherein each of the vacuum force and the irrigation force travels between the proximal compartment and the distal compartment by way of a lumen extending a length of an inner shaft that is disposed within the outer shaft.

19. The method of claim 18, further comprising advancing the inner shaft distally within the outer shaft to couple an end effector to the outer shaft.

* * * * *